(12) United States Patent
Shetty et al.

(10) Patent No.: US 11,028,866 B2
(45) Date of Patent: Jun. 8, 2021

(54) MONITOR WITH HANDLE AND IV POLE CHANNEL

(71) Applicant: Spacelabs Healthcare LLC, Snoqualmie, WA (US)

(72) Inventors: Nityanand Shetty, Sammamish, WA (US); Christina Louise Mason, Renton, WA (US); Gary Ninneman, Sammamish, WA (US); Nicholas Ong, Bellevue, WA (US); David Myers, Kennewick, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 781 days.

(21) Appl. No.: 15/573,985

(22) PCT Filed: May 26, 2016

(86) PCT No.: PCT/US2016/034324
§ 371 (c)(1),
(2) Date: Nov. 14, 2017

(87) PCT Pub. No.: WO2016/196193
PCT Pub. Date: Dec. 8, 2016

(65) Prior Publication Data
US 2018/0291939 A1    Oct. 11, 2018

Related U.S. Application Data

(60) Provisional application No. 62/168,520, filed on May 29, 2015.

(51) Int. Cl.
*F16B 9/02* (2006.01)
*F16M 13/02* (2006.01)
(Continued)

(52) U.S. Cl.
CPC ............ *F16B 9/023* (2013.01); *A61B 50/20* (2016.02); *A61B 90/92* (2016.02); *F16M 11/041* (2013.01);
(Continued)

(58) Field of Classification Search
CPC ..... F16B 9/0236; F16M 11/041; F16M 11/16; F16M 11/24; F16M 13/022;
(Continued)

(56) References Cited

U.S. PATENT DOCUMENTS 4,674,722 A * 6/1987 Danby ................... F16M 11/16
248/231.31
4,844,397 A * 7/1989 Skakoon ............. A61M 5/1413
248/231.71
(Continued)

FOREIGN PATENT DOCUMENTS

DE       202004010696      9/2004
WO        2008036344 A1     3/2008

OTHER PUBLICATIONS

International Search Report for PCT/US2016/34324, dated Sep. 1, 2016.
(Continued)

*Primary Examiner* — Anita M King
(74) *Attorney, Agent, or Firm* — Novel IP

(57) ABSTRACT

A patient monitor includes a clamping device on its rear surface for securely holding the monitor on an intravenous line (IV) pole. The clamping device is operated by the user with a sliding lever located on the side of the unit. The clamping mechanism has a ratcheting device to maintain the clamping force on the IV pole applied by the user with a simple one hand pull. The sliding lever has two buttons that release the clamp from the IV pole when the buttons are depressed simultaneously. The IV pole clamping system provides a simple and reliable mechanism for securely attaching the patient monitor to a stretcher IV pole or a free standing IV pole during patient transfer.

23 Claims, 16 Drawing Sheets

(51) Int. Cl.
*F16M 11/04* (2006.01)
*A61B 50/20* (2016.01)
*A61B 90/92* (2016.01)
*F16M 11/24* (2006.01)
*F16M 11/16* (2006.01)

(52) U.S. Cl.
CPC ............ *F16M 11/16* (2013.01); *F16M 11/24* (2013.01); *F16M 13/022* (2013.01); *A61M 2209/082* (2013.01); *F16M 2200/022* (2013.01); *F16M 2200/027* (2013.01)

(58) Field of Classification Search
CPC ........ F16M 2200/022; F16M 2200/027; A61B 50/20; A61B 90/92; A61M 2209/082; A61M 5/1415
See application file for complete search history.

(56) References Cited

U.S. PATENT DOCUMENTS

| | | | |
|---|---|---|---|
| 5,169,106 A * | 12/1992 | Rasmussen | A47B 57/26 248/230.3 |
| 5,219,428 A * | 6/1993 | Stern | A61M 5/1415 248/231.41 |
| 5,332,184 A | 7/1994 | Davis | |
| 5,829,723 A | 11/1998 | Brunner | |
| 6,247,674 B1 | 6/2001 | Jawidzik | |
| 6,382,576 B1 * | 5/2002 | Heimbrock | A61B 90/50 248/226.11 |
| 7,712,713 B2 | 5/2010 | Kankkunen | |
| 7,777,995 B2 | 8/2010 | Malkus | |
| 7,866,617 B2 * | 1/2011 | Kleitsch | A61M 5/1417 248/230.3 |
| 8,167,259 B2 * | 5/2012 | Spang, Jr. | A61M 39/283 248/230.4 |
| 9,131,904 B2 * | 9/2015 | Qualey | A61B 5/742 |
| 9,469,438 B2 * | 10/2016 | Nool | A61G 13/101 |
| 2002/0180661 A1 | 12/2002 | An | |
| 2003/0070236 A1 | 4/2003 | Barker | |
| 2007/0159772 A1 | 7/2007 | Morice | |
| 2008/0173784 A1 | 7/2008 | Mason | |
| 2009/0046402 A1 * | 2/2009 | Malkus | H01R 25/003 361/87 |
| 2010/0252702 A1 * | 10/2010 | Spang, Jr. | A61M 39/283 248/219.4 |
| 2010/0258690 A1 | 10/2010 | Kleitsch | |
| 2014/0217254 A1 | 8/2014 | Zhang | |
| 2014/0224953 A1 | 8/2014 | Quijano | |

OTHER PUBLICATIONS

Written Opinion of the International Searching Authority for PCT/US16/34324, dated Sep. 1, 2016.

* cited by examiner

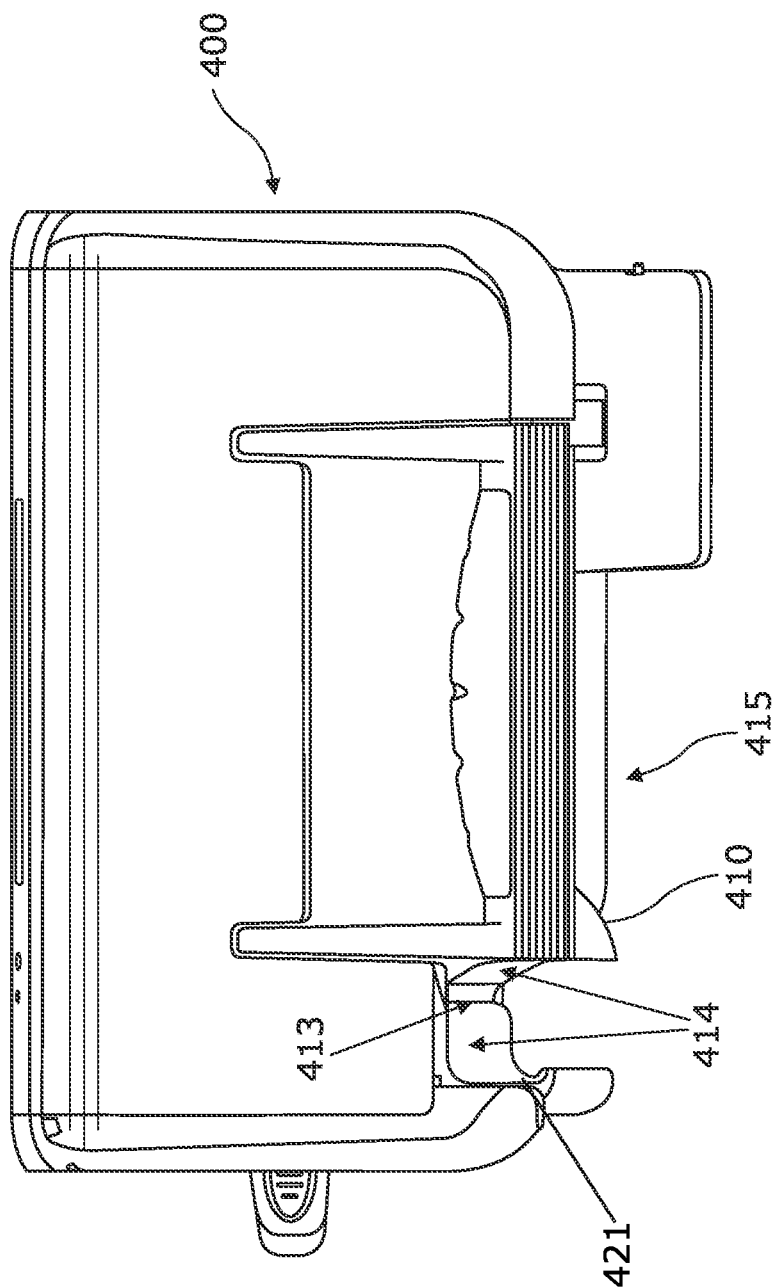

MONITOR WITH HANDLE AND IV POLE CHANNEL

CROSS-REFERENCE

The present application is a 371 National Stage application of PCT/US2016/034324, entitled "Monitor with Handle and IV Pole Channel" and filed on May 26, 2016, which relies on U.S. Patent Provisional Application No. 62/168,520, entitled "Monitor With Handle and IV Pole Channel", filed on May 29, 2015, for priority. Both of the above referenced applications are incorporated herein by reference in their entirety.

FIELD

The present specification relates generally to patient monitoring systems. More particularly, the present specification relates to a patient monitor having a handle and a slot configured with a ratcheting clamp mechanism for securely fixing the monitor to an intravenous line pole.

BACKGROUND

A patient monitoring system is an electronic medical device that measures a patient's various vital signs, collects and processes all measurements as data, and then displays the data graphically and/or numerically on a viewing screen. Graphical data is displayed continuously as data channels on a time axis (waveforms). Patient monitoring systems are positioned near hospital beds, typically in critical care units, where they continually monitor patient status via measuring devices attached to the patient and can be viewed by hospital personnel. The systems are typically positioned on a shelf, attached to the bed, or attached to a wall. Some patient monitoring systems can only be viewed on a local display, whereas others are coupled to a network and thereby display data at other locations, such as central monitoring room or nurses' stations.

Portable patient monitoring systems are available for use by emergency medical services (EMS) personnel. These systems typically include a defibrillator along with the monitor. Other portable units, such as Holter monitors, are worn by patients for a particular time period and are then returned to the physician for evaluation of the measured and collected data. Current patient monitoring systems are able to measure and display a variety of vital signs, including, pulse oximetry ($SpO_2$), electrocardiograph (ECG), invasive blood pressure (IBP), non-invasive blood pressure (NIBP), electroencephalograph (EEG), body temperature, cardiac output, capnography ($CO_2$), and respiration. Patient monitoring systems are capable of measuring and displaying maximum, minimum, and average values and frequencies of various vital parameters such as pulse and respiratory rates. Data collected can be transmitted through fixed wire connections or wireless data communication. Power to patient monitoring systems can be supplied through a main power line or by batteries. While current patient monitoring systems are effective in monitoring patient conditions and notifying medical personnel of changes, they are not without certain drawbacks and limitations.

For example, conventional patient monitoring systems are generally large, bulky machines that cannot be transported easily. Such machines are difficult to use in ambulatory or mobile situations, resulting in temporary interruption of monitoring while the patient is being transferred from one location to another. Some patient monitors are portable and systems do exist for transporting the patient monitor with the patient to and from various locations. For example, U.S. Pat. No. 7,712,713, assigned to General Electric Company, discloses a "means for fastening a patient monitor to a supporting structure, the fastening means comprising: a clamp member to be fastened about a supporting structure, the supporting structure being situated between two legs of said clamp member; tightening means for fastening said clamp member against the supporting structure, said tightening means extending through only one of said legs to fasten the supporting structure against the other of said legs; said two legs facing each other to form a slot between said two legs, said slot being wider at a bottom end than at an area between said two legs; a base member for supporting the patient monitor; a turning element and a locking element for mounting said base member to said clamp member, wherein said base member can be turned or rotated around a vertical axle with respect to the clamp member, wherein the clamp member comprises a plurality of reinforcing pins that adjoin the legs at a joint that forms the slot between the lens that receives the support structure therein, wherein the turning element is secured at the joint between the lens so that the base member rotates about the vertical axis in a plane that is perpendicular to the legs of the clamp member, wherein an outer periphery of the turning element is configured with a plurality of recesses that cooperate with the locking element to prevent turning movement of the base member, wherein the tightening means comprises a screw member and a tightening surface element configured with an insulating material that is coupled to the screw member so that actuation of the screw member in a direction perpendicular to the supporting structure in the slot translates the insulating material inside of the slot so as to place the supporting structure in contact with the insulating material and one of a pair of insulating material layers disposed on a surface of the legs inside of the slot, and wherein the patient monitor is electrically isolated from the supporting structure."

Often times, patients are transferred from one hospital unit to another, for example, for diagnostic procedures or treatment. Typically, these patients have an intravenous line in place for the administration of fluids and medications. The intravenous line is attached to a fluid reservoir, such as a saline bag, for delivery to the patient. The saline bag is usually hung from an intravenous pole, or IV pole, and the fluids are slowly administered, i.e., via a saline drip, to the patient. The IV pole can be attached to the patient's bed or is independently positioned with its own base and wheels. The IV pole provides an ideal location for securing a patient monitor during patient transfer. An IV pole is better suited for supporting the patient monitor than the patient bed, where the space is limited due to the patient and the monitor is unsecured and can fall, or the bed rails, where the patient monitor can increase the dimensions of the patient bed and can be damaged through contact with the hospital walls during transport.

Therefore, a need exists for a patient monitor having features which enable it to be securely fixed to an IV pole during patient transport. Such a patient monitor will also include a mechanism for quickly and reliably attaching the monitor to, and removing the monitor from, the IV pole.

SUMMARY

In some embodiments, the present specification discloses a patient monitor adapted to receive an intravenous line (IV) pole comprising: a housing defined by a front surface, a right surface, a left surface, and a rear surface, wherein the rear surface has a vertical length; a pair of opposing arms extending at least partially along the vertical length of the rear surface, wherein the pair of opposing arms define a channel adapted to receive said IV pole; a sliding lever positioned on the right surface of the housing, wherein the channel is positioned closer to the right surface than to the left surface; a ratcheting mechanism connected to the sliding lever and configured such that movement of the sliding lever causes said ratcheting mechanism to move horizontally; a link attached to the ratcheting mechanism such that movement of the ratcheting mechanism causes said link to move; and a clamping device attached to the link, wherein the clamping device comprises a clamping arm positioned within said channel and an extension that is connected to the link, wherein movement of the link causes the clamping arm to move from an open position to a closed position such that in said closed position the clamping arm grips said IV pole within said channel.

Optionally, the sliding lever is adapted to move horizontally and, upon moving horizontally, causes the ratcheting mechanism to move horizontally.

Optionally, the clamping arm and extension are configured to rotate about an axis such that movement of the extension causes it to rotate about the axis which, in turn, causes the clamping arm to rotate about the axis.

Optionally, said sliding lever comprises at least two buttons which are used to unlock said sliding lever and release the clamping arm such that it is in an open position.

Optionally, the inner walls of said channel comprise a layer of an elastomeric material.

Optionally, said elastomeric material has a shore hardness in a range of 70-90.

Optionally, said ratcheting system comprises a gear rack which is coupled to a pawl through a rotary damper. Optionally, said pawl engages a plurality of teeth of the gear rack and provides a ratcheting action. Optionally, said pawl has a tip configured such that it can move over the plurality of teeth of the gear rack in one direction when the sliding lever is pulled, but lock into the plurality of teeth of the gear rack when moved in an opposing direction.

Optionally, said channel has a diameter in a range of approximately 16 mm to 28 mm for receiving the IV pole.

Optionally, the pair of opposing arms have a vertical length that is equal to at least 50% of the vertical length of the rear surface.

Optionally, the channel has a vertical length that is equal to at least 50% of the vertical length of the rear surface.

Optionally, one of the pair of opposing arms is defined by the right surface of the housing.

In some embodiments, the present specification is directed toward a patient monitor adapted to receive an intravenous line (IV) pole comprising: a housing defined by a front surface, a right surface, a left surface, and a rear surface, wherein the rear surface has a vertical length; a pair of opposing arms extending at least partially along the vertical length of the rear surface, wherein the pair of opposing arms define a channel adapted to receive said IV pole; a sliding lever positioned on the left surface of the housing, wherein the channel is positioned closer to the left surface than to the right surface; a ratcheting mechanism connected to the sliding lever and configured such that movement of the sliding lever causes said ratcheting mechanism to move horizontally; a link attached to the ratcheting mechanism such that movement of the ratcheting mechanism causes said link to move; and a clamping device attached to the link, wherein the clamping device comprises a clamping arm positioned within said channel and an extension that is connected to the link, wherein movement of the link causes the clamping arm to move from an open position to a closed position such that in said closed position the clamping arm grips said IV pole within said channel.

Optionally, the clamping arm and extension are configured to rotate about an axis such that movement of the extension causes it to rotate about the axis which, in turn, causes the clamping arm to rotate about the axis.

Optionally, the sliding lever comprises at least two buttons which are used to unlock said sliding lever and release the clamping arm such that it is in an open position.

Optionally, the inner walls of said channel comprise a layer of an elastomeric material and wherein said elastomeric material has a shore hardness in a range of 70-90.

Optionally, said ratcheting system comprises a gear rack which is coupled to a pawl through a rotary damper.

Optionally, said pawl engages a plurality of teeth of the gear rack and provides a ratcheting action.

Optionally, said channel has a diameter in a range of approximately 16 mm to 28 mm for receiving the IV pole.

Optionally, the pair of opposing arms have a vertical length that is equal to at least 50% of the vertical length of the rear surface.

Optionally, the channel has a vertical length that is equal to at least 50% of the vertical length of the rear surface.

Optionally, one of the pair of opposing arms is defined by the left surface of the housing.

In some embodiments, the present specification discloses a patient monitor comprising: a channel, positioned on a rear surface of the monitor and configured to receive an intravenous line (IV) pole; and a handle which, upon closing, creates a friction fit between an elastomer layer positioned on the handle and the pole, wherein the friction fit, in combination with the IV pole positioned within the channel, is capable of maintaining a monitor elevated off the ground.

Optionally, said elastomer layer extends around a perimeter of the front surface of said monitor. Still optionally, said elastomer layer extends approximately 0.5 cm to 1.5 cm beyond a left, right, and bottom surface of said monitor. Optionally, a portion of said elastomer layer is formed in the shape of a hook and said elastomer layer of said handle and said hook define an opening for receiving said pole.

Optionally, said opening has a diameter in a range of approximately 16 mm to 22 mm for receiving an IV pole having a diameter in a range of approximately 18 mm to 24 mm.

Optionally, said opening has a diameter of approximately 20 mm.

Optionally, the monitor further comprises a groove proximate a bottom surface of said rear surface of said monitor, wherein said groove is configured to receive said pole.

Optionally, the monitor further comprises a second elastomer layer positioned horizontally along said rear surface of said monitor wherein said groove is formed in said second elastomer layer. Optionally, said second elastomer layer extends approximately 0.5 cm to 1.5 cm outwardly from said rear surface of said monitor.

Optionally, said channel and said groove are aligned vertically.

Optionally, said handle is movable from a first vertical position for carrying said monitor to a second horizontal position to create said friction fit.

Optionally, said elastomer layer has a shore hardness in a range of 70-90.

Optionally, said monitor can be mounted in a vertical position on said pole ranging from one inch off the ground to substantially the top of said pole.

Optionally, said monitor comprises a screen having a length ranging from 6 inches to 10 inches.

Optionally, said monitor comprises a customizable color band surrounding a display on a front surface of said monitor.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 4A is a top view of a patient monitor illustrating the configuration of IV pole channel in accordance with an embodiment of the present specification;

DETAILED DESCRIPTION

The present specification discloses a patient monitor having a vertical channel formed on its rear surface for receiving and securely holding an intravenous line (IV) pole. In an embodiment, the monitor also includes a ratcheting mechanism coupled to a clamping mechanism for maintaining a clamping force on the IV pole, and a sliding lever with release buttons for opening and closing a clamping mechanism. The monitor also includes a handle on its top surface which, when folded down into a horizontal position, comes into physical contact with said IV pole to assist in securing the monitor to the pole. The top surface of the monitor includes a hook configured to receive the IV pole and function in conjunction with the handle to securely fix the monitor to the IV pole. The bottom surface of the monitor includes a groove for receiving the IV pole and properly aligning the monitor in a vertical orientation in relation to the pole.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. It should be noted herein that any feature or component described in association with a specific embodiment may be used and implemented with any other embodiment unless clearly indicated otherwise.

Figure 1A:
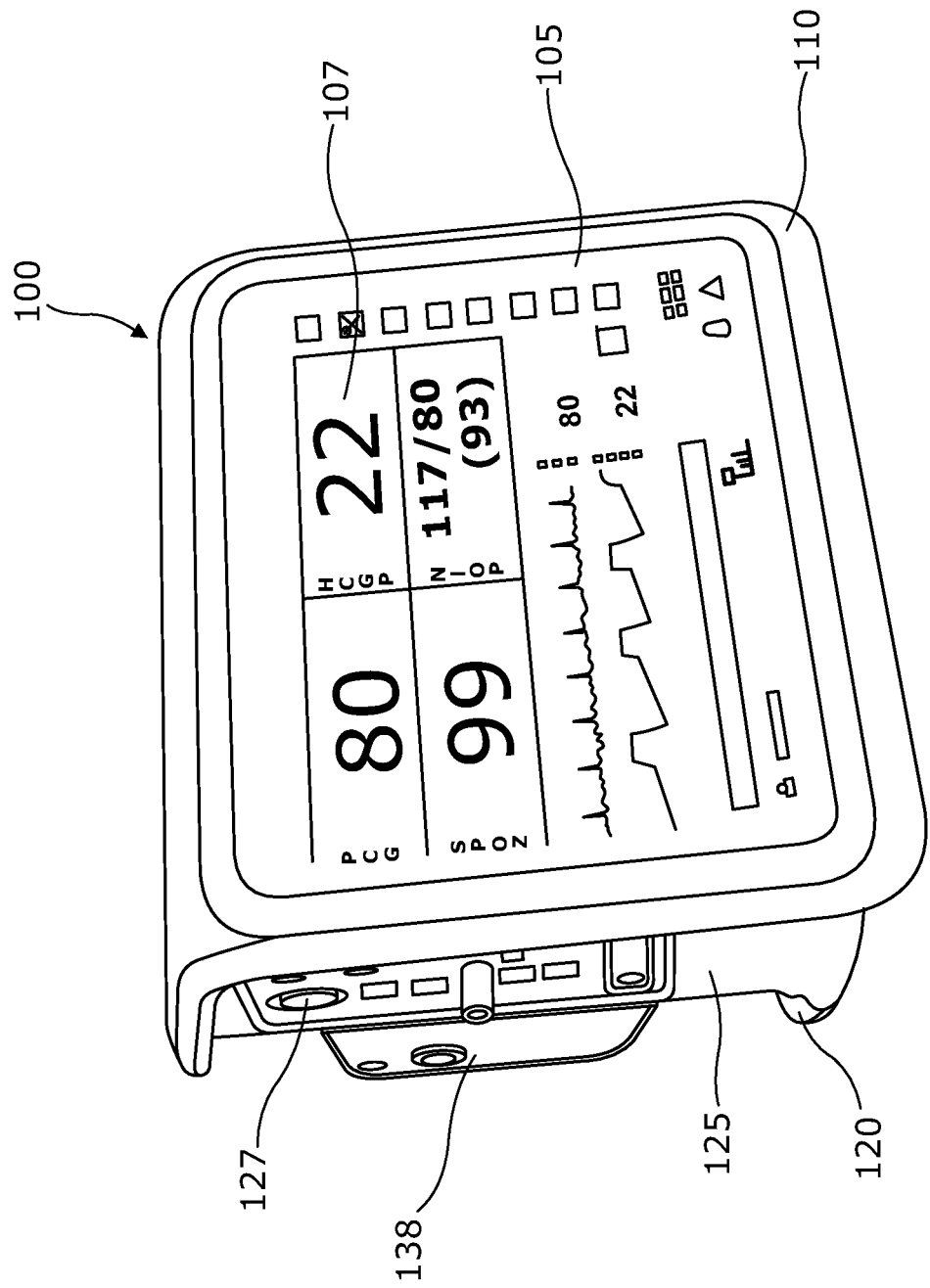
FIG. 1A is an illustration of an embodiment of a patient monitor, depicting a front surface of the monitor.

FIG. 1A is an illustration of an embodiment of a patient monitor 100, depicting the front surface 105 of the monitor 100. The front surface 105 includes a display with a plurality of LED indicators 107 for displaying patient information to hospital personnel. In an embodiment, the front surface 105 also includes a front edge cushion 110 extending along its perimeter. In some embodiments, the front edge cushion 110 is rubberized. In some embodiments, the front edge cushion 110 extends approximately 0.5 cm to 1.5 cm beyond a left, right, and bottom surface of the monitor 100. In an embodiment, the top edge of the front surface 105 is formed at an angle such that it extends horizontally toward the rear of the monitor 100 as discussed in further detail with reference to FIGS. 1B and 1C. A left surface 125 of the monitor 100 includes a plurality of ports 127 for connecting various patient parameter measuring devices. A supplemental module 138 is depicted attached to a rear surface of the monitor 100 behind said left surface 125. A rear edge cushion 120 extending along said rear surface of the monitor 100 is partially visible. In some embodiments, the rear edge cushion 120 is rubberized.

Figure 1B:
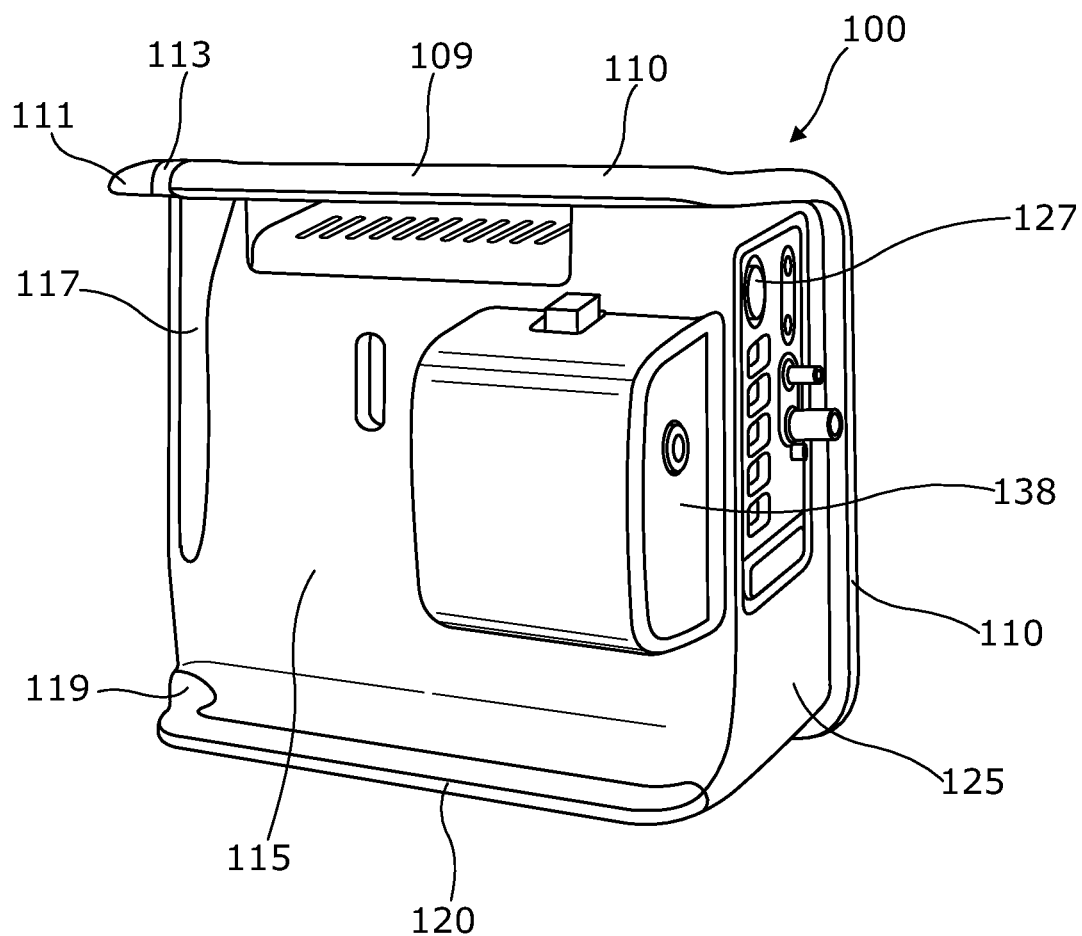
FIG. 1B is an illustration of the embodiment of the patient monitor of FIG. 1A, depicting a rear surface of the monitor.

FIG. 1B is an illustration of the embodiment of the patient monitor 100 of FIG. 1A, depicting the rear surface 115 of the monitor 100. In an embodiment, the rear surface 115 includes a rear edge cushion 120 extending outwardly from, and along a horizontal plane of, said rear surface 115. In some embodiments, the rear edge cushion 120 is rubberized. In various embodiments, the rear cushion 120 extends approximately 0.5 cm to 1.5 cm outwardly from said rear surface 115. In some embodiments, the rear cushion 120 extends along the entire width of the rear surface 115. In other embodiments, the rear cushion 120 extends along only a portion of the rear surface 115. In the embodiment pictured in FIG. 1B, the rear surface 115 includes a cutout or groove 119 positioned in the rear cushion 120. The groove 119 is configured to receive an intravenous line (IV) pole. In an embodiment, as depicted in FIG. 1B, the groove 119 is positioned proximate a right surface (when viewed from the front) of the monitor 100, while the left surface 125 (when viewed from the front) includes ports 127 for the connection of various patient parameter measuring devices. In an embodiment, the rear surface 115 also includes a channel 117 for receiving the IV pole. In an embodiment, the channel 117 extends in a vertical plane along the rear surface 115 of the monitor and, in some embodiments, is perpendicular to the rear cushion 120. In an embodiment, as depicted in FIG. 1B, the channel 117 is positioned proximate a right surface (when viewed from the front) of the monitor 100 and is aligned vertically with the groove 119. In some embodiments, the channel 117 extends along the entire length of the rear surface 115 and ends at the groove 119. In other embodiments, the channel 117 extends along only a portion of the length of the rear surface 115. In some embodiments, the channel 117 is rubberized. In an embodiment, the rear surface 115 also includes a supplemental module 138 attached thereto.

As discussed with reference to FIG. 1A, in an embodiment, the top edge of the front surface of the monitor 100 is formed at an angle to extend horizontally in the direction of the rear surface 115 such that the front edge cushion 110 continues in a path aligned with said rear surface 115 and parallel to the rear edge cushion 120. In an embodiment, the top surface of the monitor 100 comprises a handle 109 which in FIG. 1B is depicted folded down in a horizontal position. In an embodiment, the front edge cushion 110 continues along the outer edge of said handle 109. In an embodiment, the rear surface 115 further includes a hook 111 formed from said front edge cushion 110 and positioned proximate the right surface of said monitor 100. The hook 111 and a portion of the front edge cushion 110 on said handle 109 define an opening 113 configured to snugly receive an IV pole. In various embodiments, the opening 113 has a diameter in a range of approximately 16 mm to 28 mm to accommodate IV poles having a diameter between approximately 18 mm and 25 mm. In an embodiment, the opening 113 has a diameter of approximately 20 mm. Once positioned, an IV pole extends through said opening 113, along said channel 117, and within said groove 119. Though the embodiment of FIG. 1B depicts the hook 111, opening 113, channel 117, and groove 119 proximate said right side of said monitor 100, in some embodiments, these components are positioned in vertical alignment with one another along other horizontal locations across the rear surface 115 of the monitor 100. For example, in an embodiment, the hook 111, opening 113, channel 117, and groove 119 are positioned proximate the left surface of the monitor. In another embodiment, the hook 111, opening 113, channel 117, and groove 119 are positioned proximate a horizontal midpoint of the rear surface of the monitor.

Figure 1C:
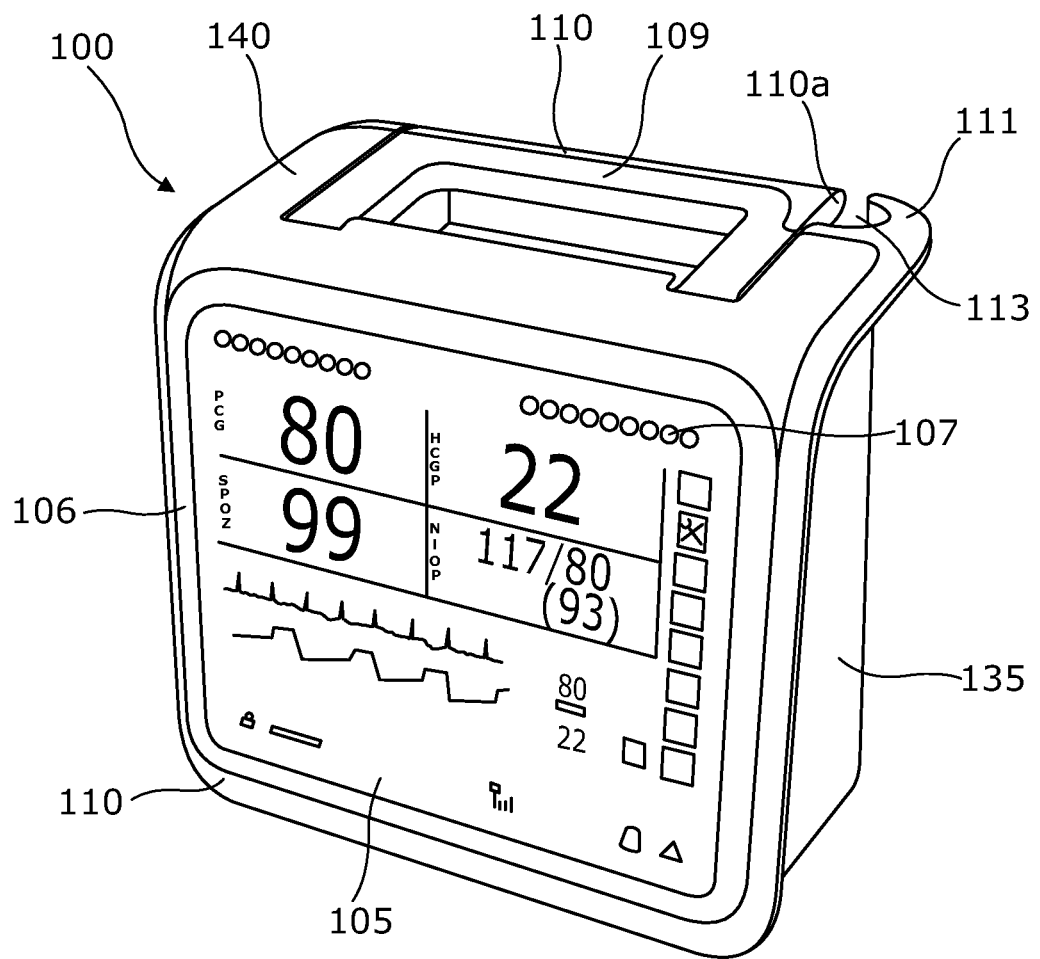
FIG. 1C is an illustration of the embodiment of the patient monitor of FIG. 1A, depicting a front surface and a top surface of the monitor.

FIG. 1C is an illustration of the embodiment of the patient monitor of FIG. 1A, depicting the front surface 105 and the top surface 140 of the monitor 100. In an embodiment the top surface 140 is a curved extension of the front surface 105 extending in a direction toward the rear of the monitor 100. The front surface 105 includes a display with a plurality of LED indicators 107 for displaying patient information. In various embodiments, the monitor 100 further comprises a customizable color band 106 surrounding the display. The color band 106 is an optional accessory used in a hospital to help identify the department to which the monitor 100 belongs based on the color coding of the band 106. The front edge cushion 110 extends along the perimeter of the front surface 105 and extends along the perimeter of the top surface 140, where it continues along an outer edge of a flip-up handle 109. In embodiments, the handle 109 can be flipped up and down from a vertical position for carrying the monitor 100 to a horizontal position, as depicted in FIG. 1C, for securing to an IV pole. A portion of the front edge cushion 110 along the top surface 140 is shaped in the form of a hook 111 proximate a right surface 135 of the monitor 100. The hook 111 and a right end portion 110a of the front edge cushion 110 of the handle 109 define an opening 113 when the handle 109 is folded down into its horizontal position. The opening 113 is configured to snugly receive an IV pole.

Figure 2A:
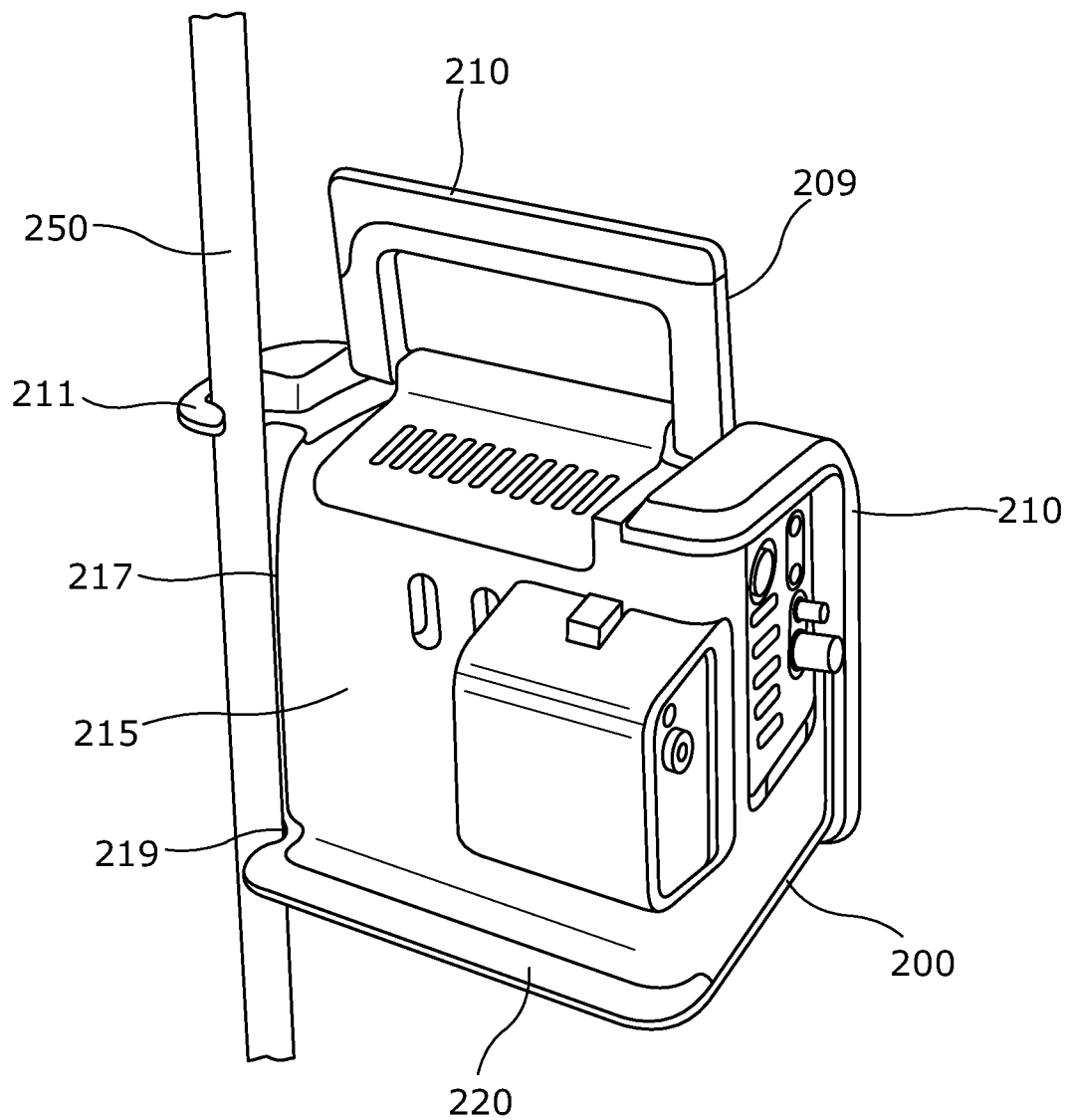
FIG. 2A is an illustration of a patient monitor attached to an intravenous line (IV) pole depicting a handle on the patient monitor in a vertical position, in accordance with an embodiment of the present specification.

FIG. 2A is an illustration of a patient monitor 200 attached to an intravenous line (IV) pole 250 depicting a handle 209 on the patient monitor 200 in a vertical position, in accordance with an embodiment of the present specification. The IV pole 250 is positioned within the channel 217 of the rear surface 215 of the monitor. An upper portion of the IV pole 250 rests within the hook 211 formed in the front edge cushion 210 and a lower portion of the IV pole 250 rests within the groove 219 formed in the rear edge cushion 220. With the handle 209 in the vertical position shown in FIG. 2A, the monitor 200 can be easily manipulated to guide the IV pole into the channel 217 of the rear surface 215 and to align the IV pole with the hook 211 and groove 219. The handle 209, in the vertical position, is also used for lifting and carrying the monitor 200.

Figure 2B:
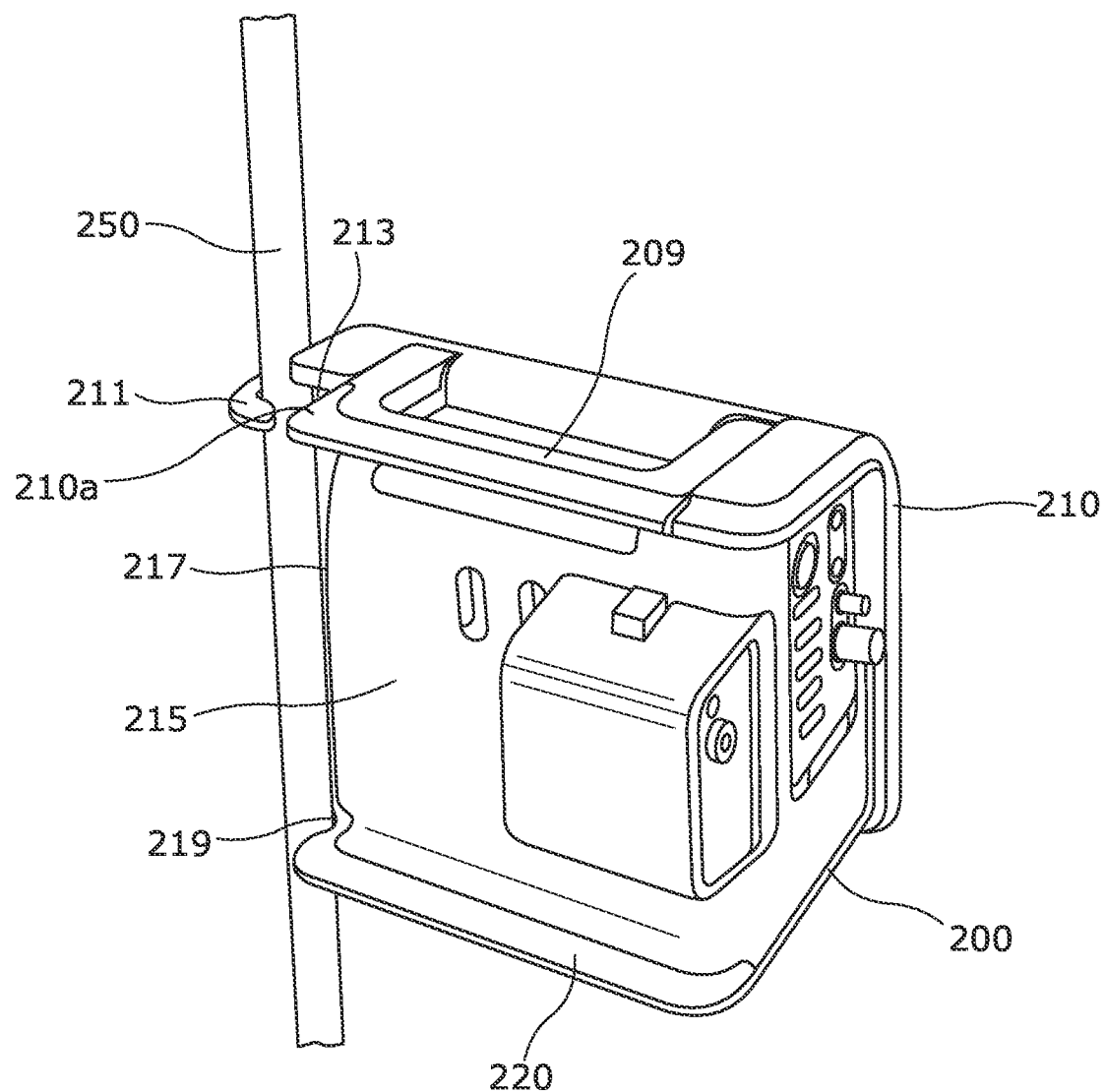
FIG. 2B is an illustration of a patient monitor attached to an IV pole depicting a handle on the patient monitor in a horizontal position, in accordance with an embodiment of the present specification.

FIG. 2B is an illustration of a patient monitor 200 attached to an IV pole 250 depicting a handle 209 on the patient monitor 200 in a horizontal position, in accordance with an embodiment of the present specification. The IV pole 250 is positioned within the channel 217 of the rear surface 215 of the monitor. An upper portion of the IV pole 250 is snugly fit within an opening 213 defined by the hook 211 and a right end portion 210a (when viewed from the front) of the front edge cushion 210 of the handle 209. A lower portion of the IV pole 250 rests within the groove 219 formed in the rear edge cushion 220. The handle 209 in the horizontal position serves to lock the IV pole 250 within the opening 213 as the hook 211 and front edge cushion portion 210a are partially compressed, providing a secure fit. The weight of the monitor 200 serves as a counter balance, maintaining the positioning of the IV pole 250 within the channel 217 and groove 219. In other words, flipping the handle 209 down creates a first lock wherein the front edge portion 210a of the handle 209 is squeezed against the IV pole 250 and the weight of the monitor 200 and the groove 219 together create a second lock wherein the weight of the monitor 200 functions as a counter balance to hold the IV pole 250 in the groove 219. To ensure that the handle 209 squeezes the IV pole 250 and creates sufficient friction, in an embodiment, the front edge cushion portion 210a is composed of an elastomer material. This latches the IV pole 250 in place within the channel 217 of the monitor 200 as well as provides a grip to avoid downward slippage of the monitor 200 on the IV pole 250. In various embodiments, the elastomer material used in the front edge cushion portion 210a has a shore hardness in a range of 70-90 and a thickness in a range of 3 mm to 12 mm. In various embodiments, any one or combination of the remainder of the front edge cushion 210, the hook 211, the channel 217, the rear edge cushion 220, and the groove 219 are composed of the same or a similar elastomer material.

In some embodiments, there is a limit to the weight and/or dimensions of a monitor which can be supported by the connection mechanism of the present specification. As discussed above the IV poles exist in different variants. The most common are those that mount onto beds or stretchers and those with their own base with wheels. The length of an IV pole mounted to a stretcher or hospital bed is typically up to 50 inches and the length of a standalone IV pole is typically up to 90 inches. For transfer, the clinician will try to mount the monitor toward the middle, or slightly higher than the middle, of the IV pole so that it's easy to remove and easy to view. Given the placement of the monitor, the monitors of the present specification will generally have a 6 inch to 10 inch screen, with dimensions ranging from 4 inch height×6 inch width to 8 inch height×10 inch width. In various embodiments, the weight of the monitor ranges from 3 pounds to 10 pounds to ensure adequate gripping force while avoiding tilting of the IV pole. In various embodiments, the monitor can be mounted at any vertical position on the IV pole from an inch above the ground level up to substantially the top of IV pole.

Figure 3A:
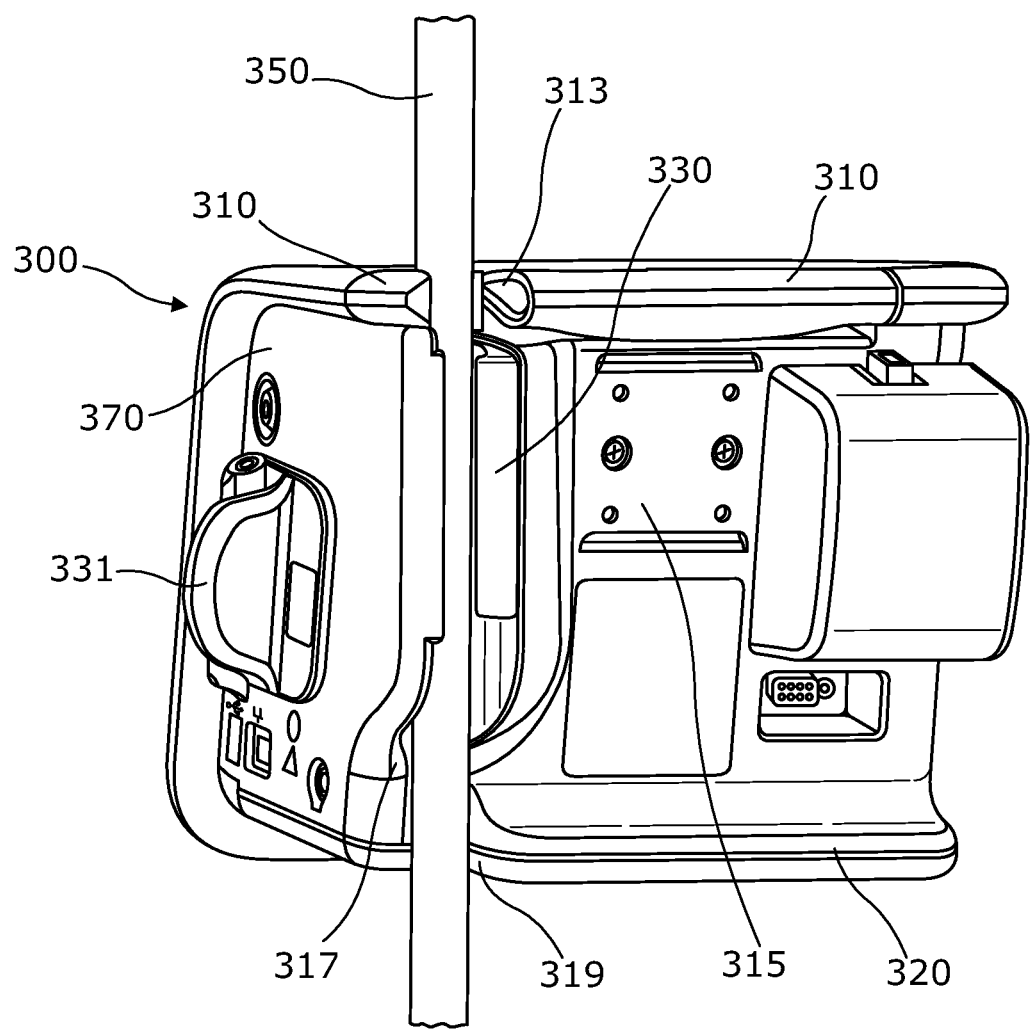
FIG. 3A illustrates a patient monitor comprising a clamping mechanism for holding the IV pole in accordance with another embodiment of the present specification.

FIG. 3A illustrates a patient monitor including a clamp and ratchet mechanism for attachment to an IV pole in accordance with another embodiment of the present specification. As shown in FIG. 3A, an IV pole 350 is positioned within a channel 317 located on the rear surface 315 of the patient monitor 300. An upper portion of the IV pole 350 is guided within an opening 313 present on the front edge cushion 310 on the rear side of the patient monitor. A lower portion of the IV pole 350 rests within the groove 319 formed in the rear edge cushion 320. In an embodiment, the present specification describes a system for securing the pole 350 in a firm position within the channel 317 with the assistance of a clamp 330 positioned within the channel 317. In an embodiment, the right side surface 370 (as viewed from the front) of the patient monitor 300 comprises a sliding lever 331 which is coupled to the clamp 330 such that as the lever 331 can be operated to control the position of the clamp 330 through a ratcheting system. In an embodiment, initially the clamp 330 is in a first or open position and once the IV pole 350 is guided into the channel 317, the lever 331 is operated to move the clamp 330 in a second or closed position. In a closed position, the clamp 330 covers a portion of the pole 350 and locks it in its position.

Figure 3B:
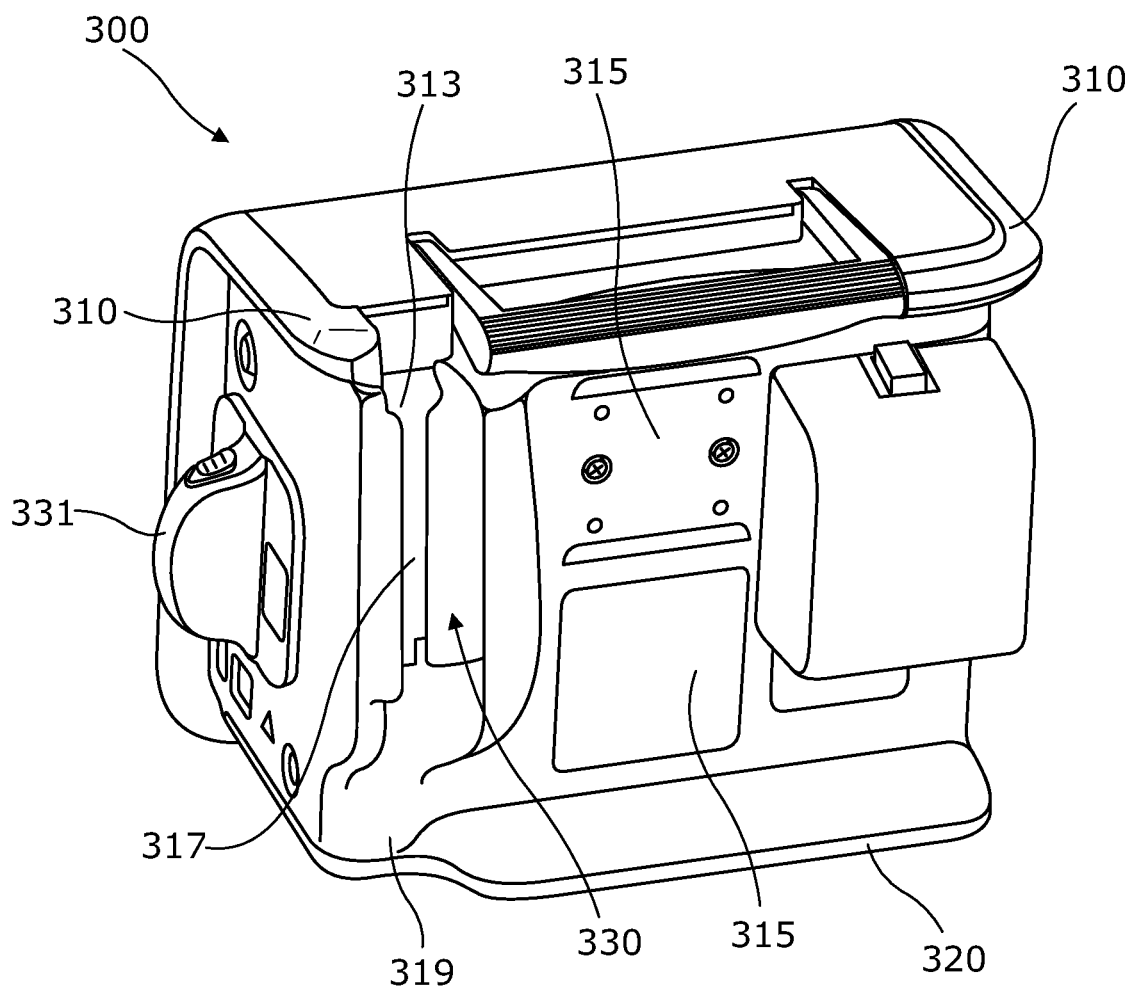
FIG. 3B illustrates a rear view of a patient monitor wherein the patient monitor is not attached to the IV pole and a clamp is in a closed position in accordance with an embodiment of the present specification.

FIG. 3B illustrates the rear view of a patient monitor without attachment to an IV pole and with the clamp on the rear side of the monitor in a closed position in accordance with an embodiment of the present specification. As shown in FIG. 3B, the rear side 315 of the patient monitor 300 comprises a channel 317 which is vertically aligned with a groove 319 formed in the rear edge cushion 320 and an opening 313 present on the front edge cushion 310 on the rear side of the patient monitor. As shown in the FIG. 3B, the system comprises a sliding lever 331 which is coupled to the clamp 330 such that as the lever 331 can be operated to control the position of the clamp 330. In a closed position, as shown in the FIG. 3B, the clamp is positioned such that it locks the IV pole in its position. The operation of the lever 331 and the clamp 330 is described in subsequent figures.

Figure 3C:
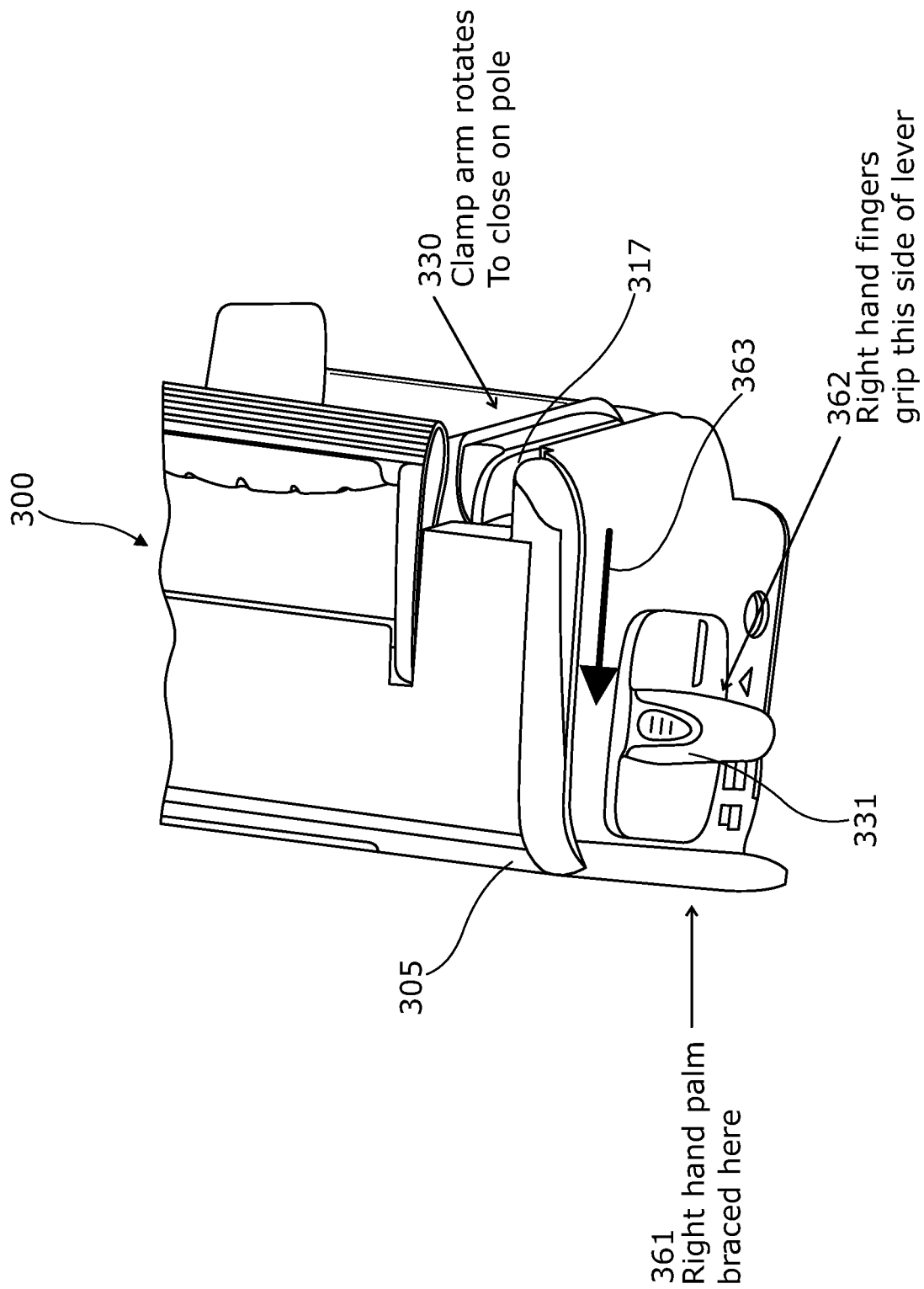
FIG. 3C illustrates the clamping mechanism in the patient monitor described in FIG. 3A in accordance with an embodiment of the present specification.

FIG. 3C illustrates the clamping mechanism of the patient monitor described in FIG. 3A in accordance with an embodiment of the present specification. In an embodiment, the sliding lever 331 is manually operated by the user to move the clamp 330 from a first (open) position to a second (closed) position. In an embodiment, the user places the palm of his hand on the right side 361 (as seen from the front) of the front portion 305 of the patient monitor 300 such that his fingers grip the sliding lever 331 at the location 362. Subsequently, the user slightly pulls the lever 331 in a direction shown by the arrow 363 and as a result the clamp 330, which is coupled to the lever 331, rotates to close in around and cover a portion of the pole that would be present in the channel 317 on the rear portion of the patient monitor 300. In an embodiment, a simple pulling motion with one hand closes the clamp on the IV pole. A ratcheting mechanism maintains the clamping force on the IV pole indefinitely until the clamp is released.

Figure 3D:
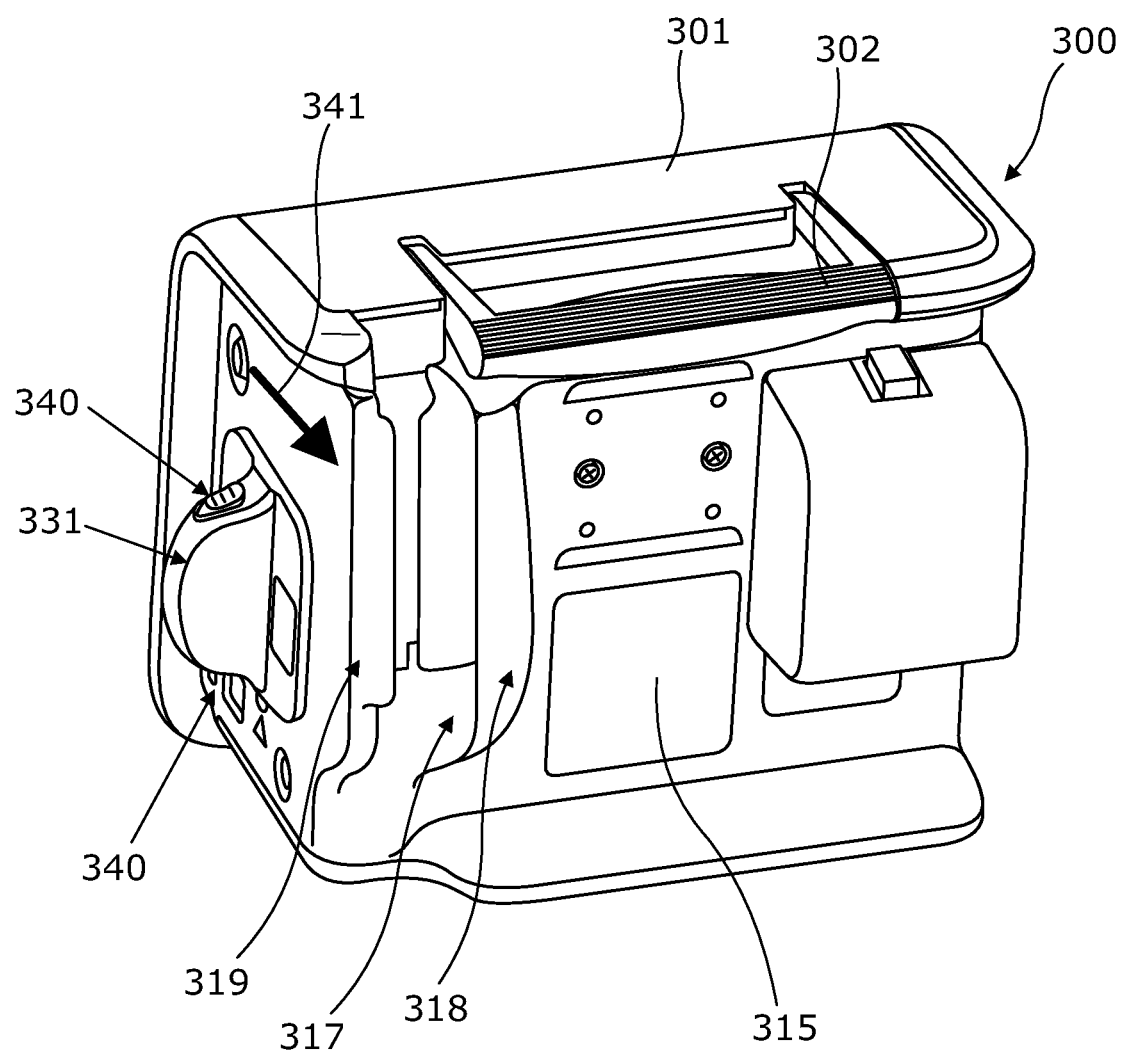
FIG. 3D illustrates a mechanism for detaching the patient monitor from an IV pole in accordance with an embodiment of the present specification.

FIG. 3D illustrates a mechanism for detaching the patient monitor described in FIG. 3A from an IV pole in accordance with an embodiment of the present specification. As shown in FIG. 3D, the patient monitor 300 comprises an IV pole channel 317 on its rear surface 315. In an embodiment, the patient monitor 300 is configured such that the clamp which is used to lock the IV pole in the channel 317 can be released by pressing a plurality of buttons In an embodiment, the system comprises buttons 340 positioned on each of the top and bottom sections of the sliding lever 331 such that to release the clamp and unlock the IV pole, the buttons 340 are depressed vertically. As the buttons 340 are depressed, the sliding lever 331 is unlocked from its position and with a slight push it slides towards the back in the direction shown by the arrow 341 which unlocks the clamp 330 (shown in FIG. 3A). In an embodiment, the system is configured such that as the clamp is unlocked, it rotates away from the IV pole and automatically retreats inside the rear portion 315. Once the clamp retreats inside the rear portion of the patient monitor, the patient monitor can be detached from the IV pole.

FIG. 4A is a top view of a patient monitor illustrating the configuration of IV pole channel in accordance with an embodiment of the present specification. As shown in FIG. 4A, the patient monitor 400 comprises an opening 413 present on the front edge cushion 410 on the rear side 415 of the patient monitor. In an embodiment, the internal walls 414 of opening 413 have an outer layer 421 comprising elastomeric material. An elastomeric material is a natural or synthetic polymer such as rubber having elastic properties. It provides a firm support to attach the patient monitor 400 to the IV pole without causing any wear and tear on its surface. In FIG. 4A, the clamp (such as 330 in FIG. 3A) that is used to grip the IV pole is in an open position resting inside the rear portion 415 of the monitor.

Figure 4B:
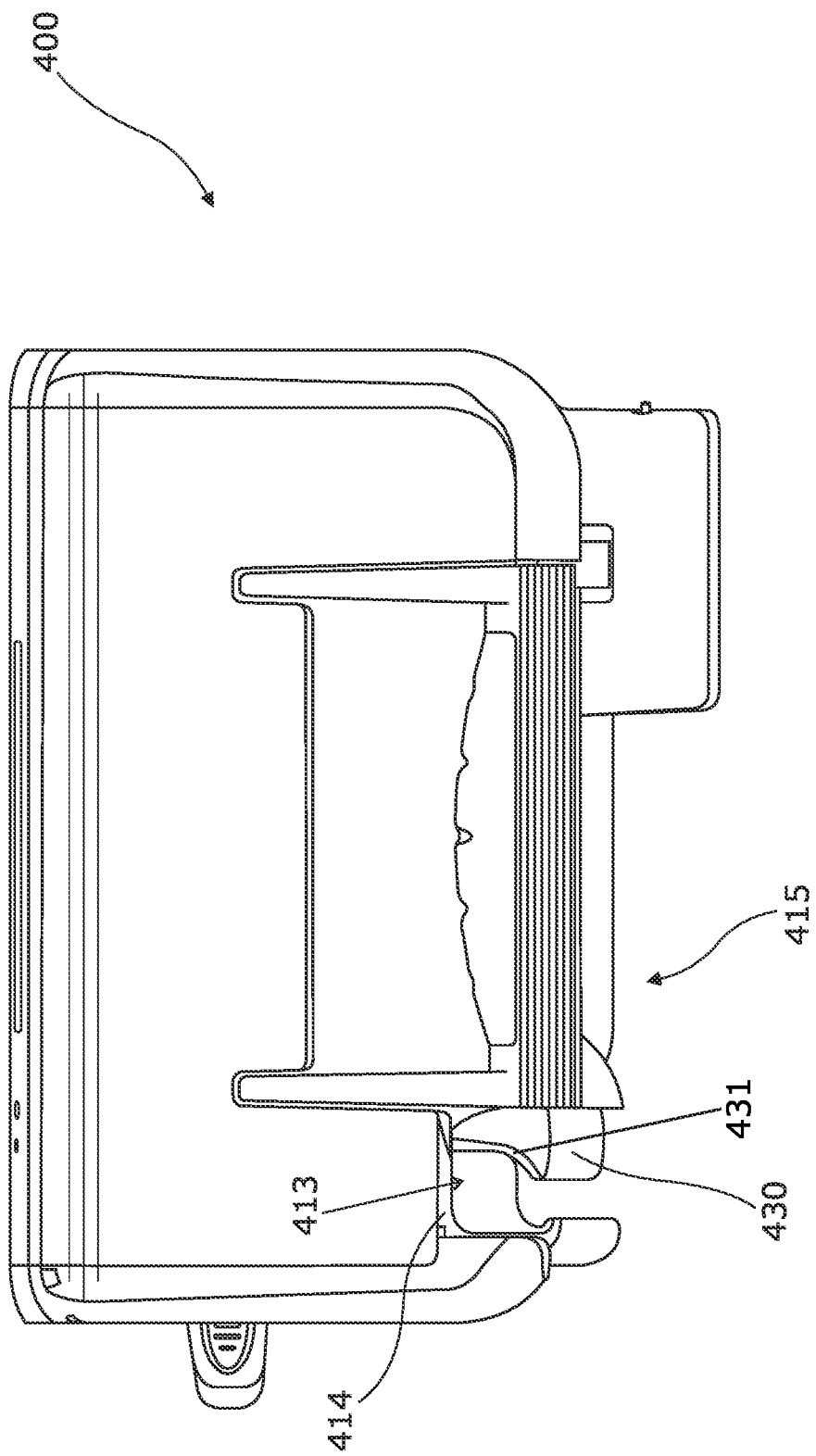
FIG. 4B is another top view of the patient monitor illustrating the clamp in an open position.

FIG. 4B illustrates another configuration of the patient monitor of FIG. 4A such that in FIG. 4B, the clamp 430 is in an open position. In an embodiment, the clamp 430 also comprises an outer layer 431 of elastomeric material to prevent any wear and tear on the surface of IV pole.

Figure 5:
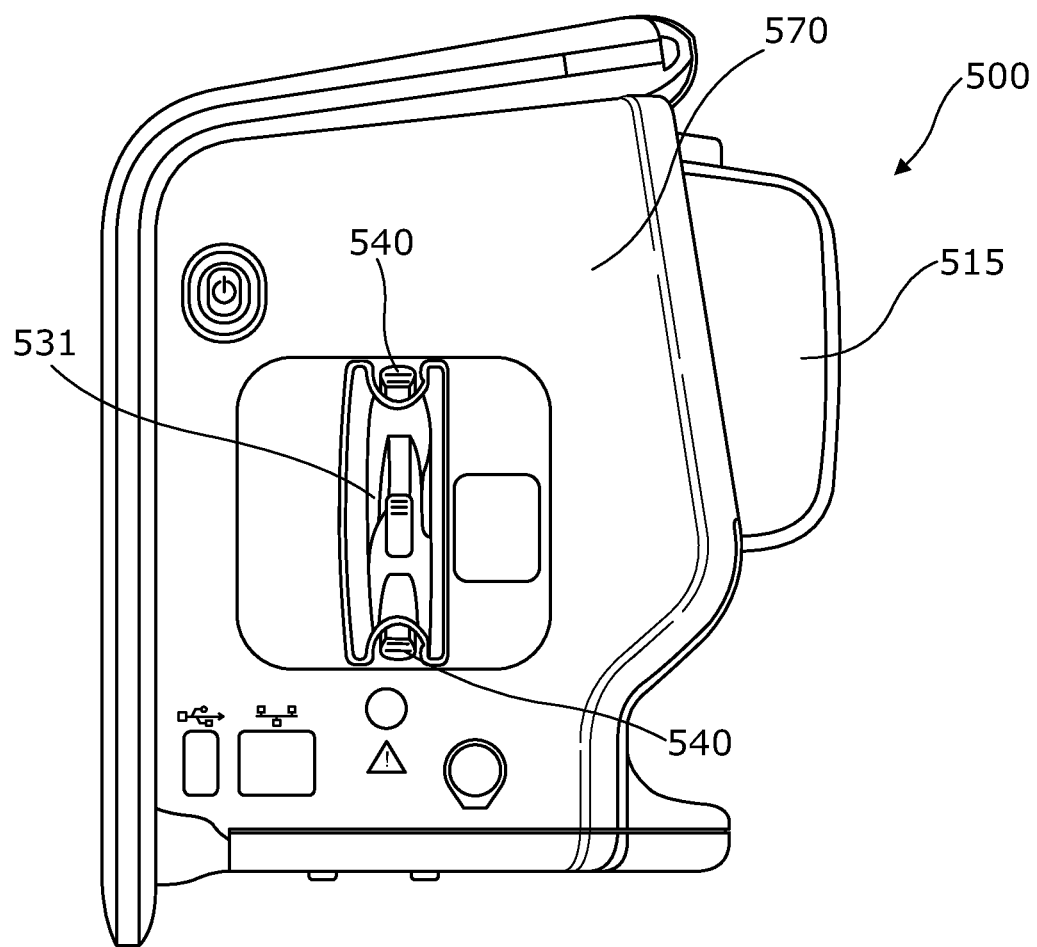
FIG. 5 is a side view of the patient monitor in accordance with an embodiment of the present specification.

FIG. 5 is a side view of the patient monitor of FIG. 3A in accordance with an embodiment of the present specification. As shown in FIG. 5, the patient monitor 500 comprises a rear portion 515 and a right side portion 570 (as viewed from the front). The side portion 570 comprises a sliding lever 531 which in an embodiment is coupled to a ratcheting clamping system, as further discussed below, such that the sliding lever 531 can be operated to open or close a clamp positioned in the IV pole channel located on the rear side 515 of the patient monitor. In an embodiment, the clamp can be moved from an open position to a closed position by slightly pulling the sliding lever 531 towards the front side of the patient monitor. Once the sliding lever 531 is moved towards the front side, a clamp emerges from inside the rear portion of the monitor and firmly grips the IV pole present in a channel located on the rear side of the monitor and the sliding lever 531 locks itself in this position.

Referring back to FIG. 3D, as previously discussed, the clamping system comprises the sliding lever 331 positioned on a right or left side of the monitor housing 301. The monitor housing 301 has a front face which comprises the display, a top surface with a handle 302 that is configured to rotate from a vertical to horizontal position, and a rear surface 315 configured to receive an IV pole. The rear surface 315 comprises a channel 317 which is preferably formed by two opposing curved arms 318, 319 extending vertically across the rear surface 315. In one embodiment the two opposing curved arms 318, 319 are positioned proximate the right side of the monitor 300 (as viewed when facing the monitor), in which case the right opposing curved arm 319 is an extension of the right side of the monitor 300 and the sliding lever 331 is positioned on the right side of the monitor 300. In one embodiment the two opposing curved arms 318, 319 are positioned proximate the left side of the monitor 300 (as viewed when facing the monitor), in which case the left opposing curved arm 319 is an extension of the left side of the monitor 300 and the sliding lever 331 is positioned on the left side of the monitor 300. In one embodiment, the two opposing curved arms 318, 319 extend the full vertical length of the monitor 300. In another embodiment, the two opposing curved arms 318, 319 extend a vertical length equal to a range from one half the full vertical length to the full vertical length of the monitor 300, and any increment therein, particularly ⅔ the full vertical length of the monitor 300.

The two opposing curved arms 318, 319 are separated from each other by a space and, together, define the channel 317. The channel 317 is generally curved, but not necessarily cylindrical. The distance across the channel 317, roughly referred to as a diameter but not necessarily indicative of a perfect cylindrical shape, is in a range of 16 mm to 28 mm. As further discussed below and referring to FIG. 6D, positioned within the channel 317 is a clamping arm 680 that, in an undeployed state, lies flush with at least one of the two opposing curved arms 318, 319 and, in a deployed state, extends into the channel 317 based upon the movement of the sliding lever 331. The vertical length of the clamping arm 680 is preferably equal to 50% or more of the vertical length of the opposing arms 318, 319. In one embodiment, the vertical length of the clamping arm is equal to the vertical length of the opposing arms 318, 319.

In an embodiment, the sliding lever 531 comprises a buttons 540 which can be depressed vertically to unlock the sliding lever 531. In an embodiment, the pair of buttons 540 are depressed vertically which unlocks the sliding lever 531 and subsequently, the sliding lever 531 is slightly pushed towards the rear side of the monitor which causes the clamp to release the IV pole and retreat inside the rear cover of the monitor.

Figure 6A:
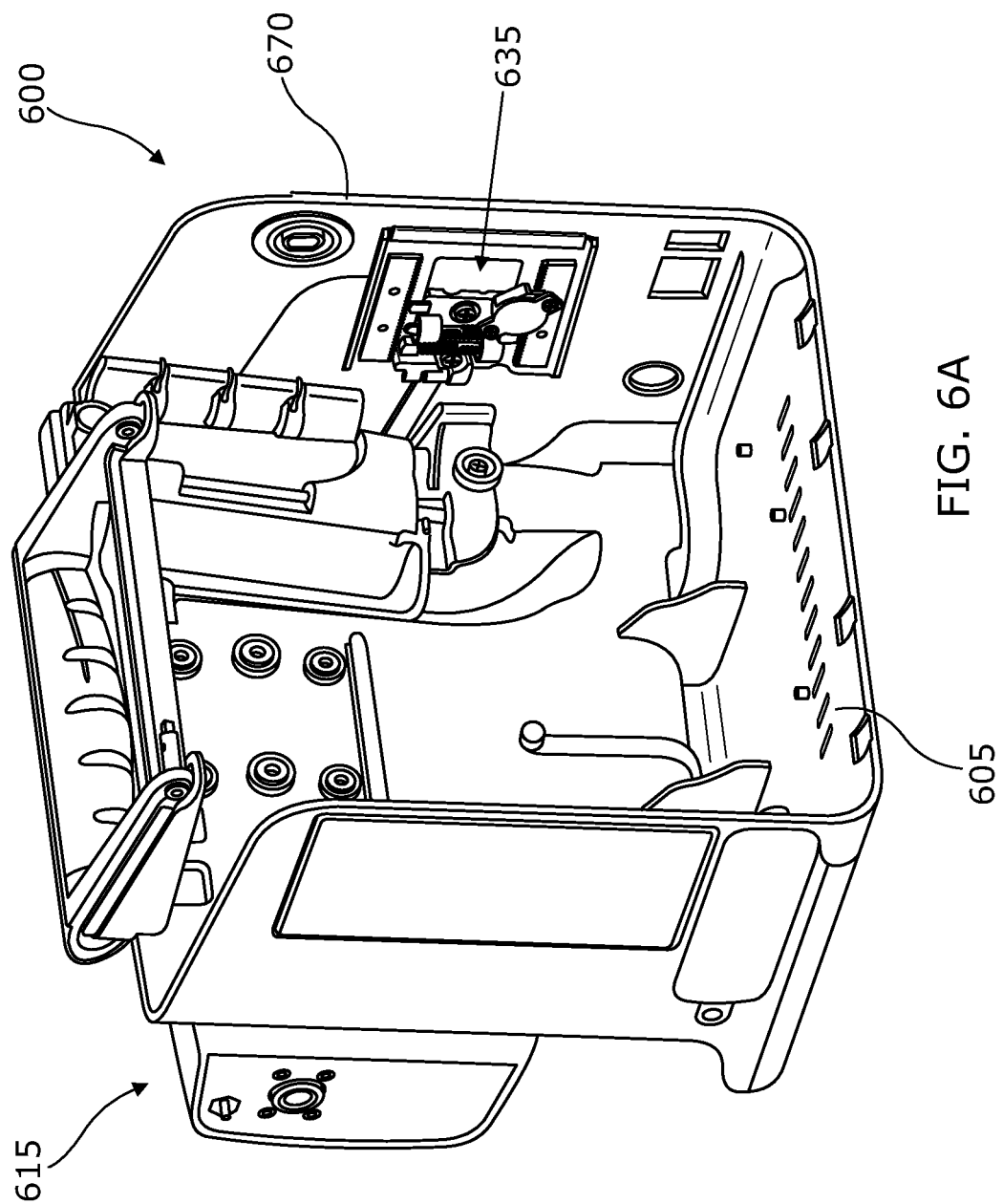
FIG. 6A is a front, internal view of the patient monitor illustrating a ratchet system used for operating the clamping mechanism described in FIG. 3A in accordance with an embodiment of the present specification.

FIG. 6A is a front, internal view of the patient monitor illustrating a ratchet system used for operating the clamping mechanism described in FIG. 3A in accordance with an embodiment of the present specification. As shown in FIG. 6A, the patient monitor 600 comprises a front section 605 and a rear section 615. In an embodiment, a right side (as viewed from the front) section 670 of the patient monitor 600 comprises a sliding lever (not shown) located on its outer surface (as also described in FIG. 3A). The sliding lever located on the outer surface of the section 670 is coupled to a ratcheting system 635 positioned on the internal surface of the section 670. The ratcheting system 635 is further coupled to a clamp which is used for securing the patient monitor 600 to an IV pole. In an embodiment, the ratcheting system 635 provides a coupling mechanism between the sliding lever and the clamp. In an embodiment, as the sliding lever is pulled towards the front side of the patient monitor, the ratcheting system 635 acts to move the clamp from an open position to a closed position and it also locks the system in this position. When the buttons present on the sliding lever are depressed vertically and the siding lever is pushed backwards, the ratcheting system acts to move the clamp from a closed position to an open position in an embodiment.

Figure 6B:
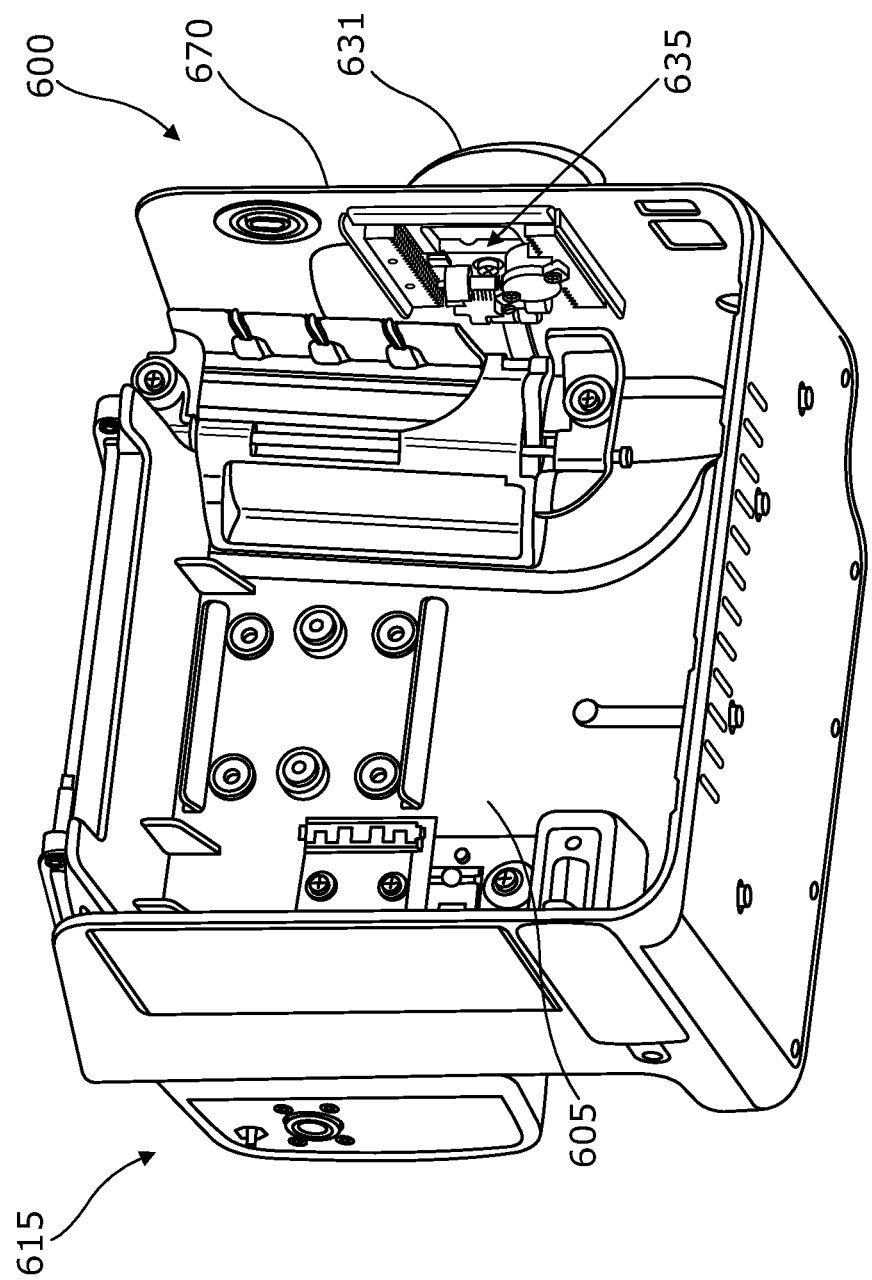
FIG. 6B is a close-up view of the internal section of the patient monitor as depicted in FIG. 6A.

FIG. 6B is a close-up view of the internal section of the patient monitor as depicted in FIG. 6A. As shown in FIG. 6B, the sliding lever 631 is positioned on the outer surface of the side section 670 such that the sliding lever 631 is coupled to the ratcheting system 635 located on the internal surface of the side section 670.

Figure 6C:
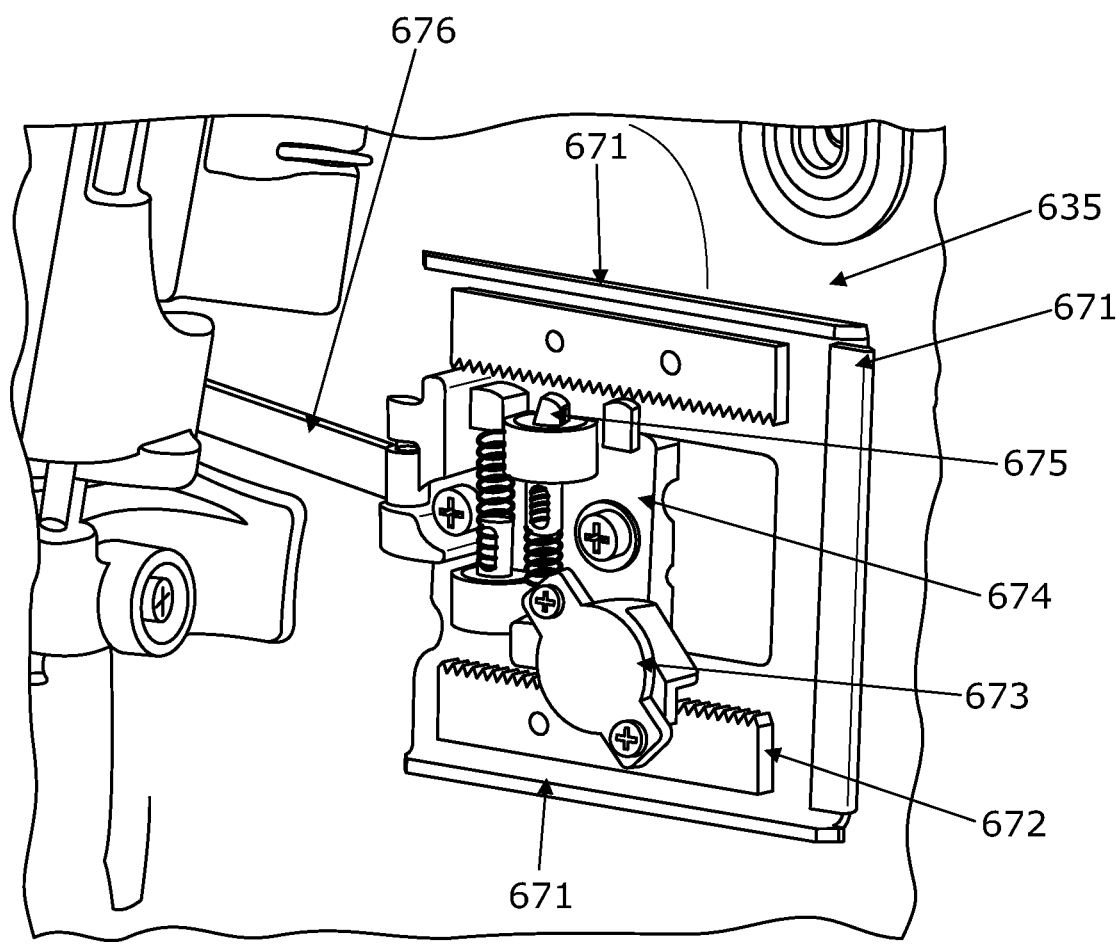
FIG. 6C is an exploded view of the ratchet system of FIG. 6A used for coupling a sliding lever to the clamp in accordance with an embodiment of the present specification.

FIG. 6C is an exploded view of the ratcheting system of FIG. 6A used for coupling a sliding lever to the clamp in accordance with an embodiment of the present specification. As shown in FIG. 6C, the ratcheting system 635 comprises a sheet metal frame 671 used to strengthen the plastic enclosure in the area of the ratcheting system. Gear racks 672 are mounted to the internal surface of the frame 671 and are stationary. A pawl 675 engages the teeth of the gear rack and provides the ratcheting action. The pawl 675 has a tip that is shaped in such a way that it can move over the teeth of the gear rack in one direction when the lever 631 is pulled, but locks into the teeth of the gear rack when moved in the opposite direction. The system comprises springs coupled to the pawl that provide the force necessary to engage the rack teeth. A plate 674 is used to act as a carriage for the ratchet components and slides horizontally in a rectangular opening in the plastic enclosure. The plate is coupled to a sheet metal link 676 that connects to the clamping arm 680. The rotary damper 673 engages the rack 672 with a gear and provides resistance to the horizontal movement. This helps to improve the "feel" of the ratchet system to the user, as well as providing resistance to rapid opening of the clamping arm when the clamping arm 680 is released. There are also levers positioned behind plate 674. When the buttons positioned on the outside surface of the monitor are pushed, the levers rotate and force the pawls to move vertically against the force of the spring to disengage the rack, which in turn releases the IV pole clamp.

Figure 6D:
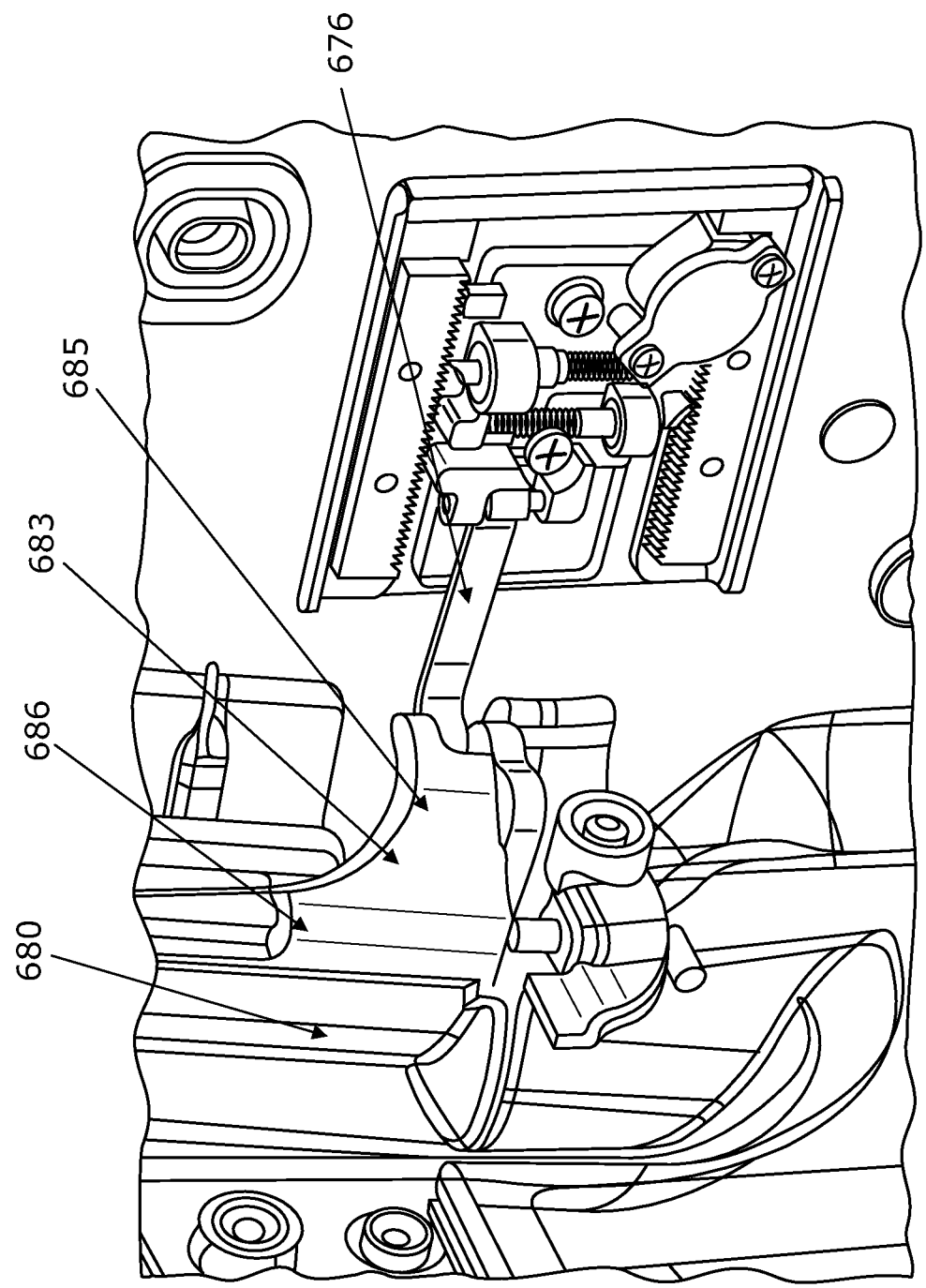
FIG. 6D is an exploded view of the clamping arm of FIG. 6A in accordance with an embodiment of the present specification.

Referring to FIG. 6D, the link 676 attaches to an extension 683 which is configured to rotate around a hinged axis point 686. The clamping arm 680 is positioned on the other side of the hinged axis point 686, relative to the extension 683 such that, when the link 676 moves the extension 683, causing it to rotate about the hinged axis point 686, that rotation is translated to the clamping arm 680, which is attached to the same hinged axis point 686 as the extension 683. In one embodiment, the extension 683 is curved at a portion 685 to better facilitate a smooth rotational motion. Accordingly, distal movement of the link, by virtue of the sliding lever and ratcheting system, causes the extension 683 to rotate clockwise about the hinged axis point 686 which, in turn, causes the clamping arm 680 to rotate clockwise and clamp down on an IV pole positioned within the channel. When operated in reverse, the proximal movement of the link, by virtue of the sliding lever and ratcheting system, causes the extension 683 to rotate counter clockwise about the hinged axis point 686 which, in turn, causes the clamping arm 680 to rotate counter clockwise and clamp down on an IV pole positioned within the channel.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A patient monitor adapted to receive an intravenous line (IV) pole comprising:
    a housing defined by a front surface, a right surface, a left surface, and a rear surface, wherein the rear surface has a vertical length;
    two opposing arms extending at least partially along the vertical length of the rear surface, wherein the two opposing arms define a channel adapted to receive said IV pole;
    a sliding lever positioned on the right surface of the housing, wherein the channel is positioned closer to the right surface than to the left surface;
    a ratcheting mechanism connected to the sliding lever and configured such that movement of the sliding lever causes said ratcheting mechanism to move horizontally;
    a link attached to the ratcheting mechanism such that movement of the ratcheting mechanism causes said link to move; and
    a clamping device attached to the link, wherein the clamping device comprises a clamping arm positioned within said channel and an extension that is connected to the link, wherein movement of the link causes the clamping arm to move from an open position to a closed position such that in said closed position the clamping arm grips said IV pole within said channel.

2. The patient monitor of claim 1 wherein the sliding lever is adapted to move horizontally and, upon moving horizontally, causes the ratcheting mechanism to move horizontally.

3. The patient monitor of claim 1 wherein the clamping arm and extension are configured to rotate about an axis such that movement of the extension causes it to rotate about the axis which, in turn, causes the clamping arm to rotate about the axis.

4. The patient monitor of claim 1, wherein said sliding lever comprises at least two buttons which are used to unlock said sliding lever and release the clamping arm such that it is in an open position.

5. The patient monitor of claim 4, wherein said channel has a diameter in a range of approximately 16 mm to 28 mm for receiving the IV pole.

6. The patient monitor of claim 1, wherein inner walls of said channel comprise a layer of an elastomeric material.

7. The patient monitor of claim 6, wherein said elastomeric material has a shore hardness in a range of 70-90.

8. The patient monitor of claim 1, wherein said ratcheting system comprises a gear rack which is coupled to a pawl through a rotary damper.

9. The patient monitor of claim 8, wherein said pawl engages a plurality of teeth of the gear rack and provides a ratcheting action.

10. The patient monitor of claim 9, wherein said pawl has a tip configured such that it can move over the plurality of teeth of the gear rack in one direction when the sliding lever is pulled, but lock into the plurality of teeth of the gear rack when moved in an opposing direction.

11. The patient monitor of claim 1, wherein the two opposing arms have a vertical length that is equal to at least 50% of the vertical length of the rear surface.

12. The patient monitor of claim 1, wherein the channel has a vertical length that is equal to at least 50% of the vertical length of the rear surface.

13. The patient monitor of claim 1, wherein one of the two opposing arms is defined by the right surface of the housing.

14. A patient monitor adapted to receive an intravenous line (IV) pole comprising:
    a housing defined by a front surface, a right surface, a left surface, and a rear surface, wherein the rear surface has a vertical length;
    two opposing arms extending at least partially along the vertical length of the rear surface, wherein the two opposing arms define a channel adapted to receive said IV pole;
    a sliding lever positioned on the left surface of the housing, wherein the channel is positioned closer to the left surface than to the right surface;
    a ratcheting mechanism connected to the sliding lever and configured such that movement of the sliding lever causes said ratcheting mechanism to move horizontally;
    a link attached to the ratcheting mechanism such that movement of the ratcheting mechanism causes said link to move; and
    a clamping device attached to the link, wherein the clamping device comprises a clamping arm positioned within said channel and an extension that is connected to the link, wherein movement of the link causes the clamping arm to move from an open position to a closed position such that in said closed position the clamping arm grips said IV pole within said channel.

15. The patient monitor of claim 14 wherein the clamping arm and extension are configured to rotate about an axis such that movement of the extension causes it to rotate about the axis which, in turn, causes the clamping arm to rotate about the axis.

16. The patient monitor of claim 14, wherein said sliding lever comprises at least two buttons which are used to unlock said sliding lever and release the clamping arm such that it is in an open position.

17. The patient monitor of claim 14, wherein inner walls of said channel comprise a layer of an elastomeric material and wherein said elastomeric material has a shore hardness in a range of 70-90.

18. The patient monitor of claim 14, wherein said ratcheting system comprises a gear rack which is coupled to a pawl through a rotary damper.

19. The patient monitor of claim 18, wherein said pawl engages a plurality of teeth of the gear rack and provides a ratcheting action.

20. The patient monitor of claim 14, wherein said channel has a diameter in a range of approximately 16 mm to 28 mm for receiving the IV pole.

21. The patient monitor of claim 14, wherein the two opposing arms have a vertical length that is equal to at least 50% of the vertical length of the rear surface.

22. The patient monitor of claim 14, wherein the channel has a vertical length that is equal to at least 50% of the vertical length of the rear surface.

23. The patient monitor of claim 14, wherein one of the two opposing arms is defined by the left surface of the housing.

* * * * *